United States Patent [19]

Hay

[11] Patent Number: 4,851,548

[45] Date of Patent: Jul. 25, 1989

[54] SUPERIOR CATALYSTS FOR PREPARATION OF 3-AMINO-2,2,4,4-TETRAMETHYLTHIETANE VIA THE LEUCKART REACTION

[75] Inventor: Bruce A. Hay, Mystic, Conn.

[73] Assignee: Pfizer Inc., New York, N.Y.

[21] Appl. No.: 180,511

[22] Filed: Apr. 12, 1988

[51] Int. Cl.$^4$ .......................................... C07D 331/04
[52] U.S. Cl. .................................................. 549/88
[58] Field of Search ......................................... 549/88

[56] References Cited

U.S. PATENT DOCUMENTS 4,411,925  10/1983  Brennan et al. ..................... 426/548

OTHER PUBLICATIONS

Slaugh et al., Chem. Abst., vol. 91, (1979), 19882q.
Moore, "Organic Reaction" V, 301–330 (1949).
Webers et al., J. Am. Chem. Soc., 70, 1422–1444 (1948).
Bunnett et al., J. Am. Chem. Soc., 71, 1587–1589 (1949).

*Primary Examiner*—Alan Siegel
*Attorney, Agent, or Firm*—Peter C. Richardson; J. Trevor Lumb; Albert E. Frost

[57] ABSTRACT

Boric acid or aluminum salts, especially aluminum chloride, aluminum sulfate and aluminum nitrate and hydrates of said salts, are superior catalysts for preparation of 3-amino-2,2,4,4-tetramethylthietane via the Leuckart reaction.

6 Claims, No Drawings

SUPERIOR CATALYSTS FOR PREPARATION OF 3-AMINO-2,2,4,4-TETRAMETHYLTHIETANE VIA THE LEUCKART REACTION

BACKGROUND OF THE INVENTION

This invention relates to an improvement in the Leuckart reaction. More particularly it relates to an improvement in said reaction, especially as it applies to the preparation of 3-amino-2,2,4,4-tetramethylthietane, the improvement comprising the use of superior catalysts; namely, aluminum salts or boric acid.

The Leuckart reaction, a process for the reductive alkylation of ammonia, primary or secondary amines with carbonyl compounds has been extensively used to prepare a wide variety of amines (Moore, Organic Reactions, V, 301–330 (1949); Moeller et al. in Houben-Weyl, Methoden der Organischen Chemie XI/I, Georg Thieme, Stuttgart, 1956, pp. 648–664). The reduction is effected by reacting a carbonyl compound and the formic acid salt or formyl derivative of ammonia or amine to be alkylated, e.g. ammonium formate or formamide.

The use of magnesium chloride as catalyst for the reaction of benzophenone with formamide was reported by Webers et al., J. Am. Chem. Soc. 70, 1422–1424 (1948).

Bunnett et al.,J Am. Chem. Soc., 71, 1587–1589 (1949), report the results of their investigation into the use of a variety of substances as catalysts in the Leuckart reaction, including ferric chloride, zinc chloride, calcium chloride and magnesium chloride. The ferric chloride and zinc chloride were inferior to magnesium chloride in the reaction of p-bromoacetophenone with dimethylformamide. Calcium chloride was, however, reported to be a better catalyst in said reaction than magnesium chloride.

SUMMARY OF THE REACTION

It has now been surprisingly found that boric acid or aluminum salts catalyze preparation of 3-amino-2,2,4,4-tetramethylthietane via the Leuckart reaction to provide a product of greatly improved quality over that produced by the use of magnesium chloride or calcium chloride as catalysts. The use of boric acid or aluminum salts and hydrates thereof as catalysts is of particular advantage in the Leuckart reaction when said reaction is used to prepare 3-amino-2,2,4,4-tetramethylthietane of value as reactants for preparation of L-aspartyl-D-alanine N-(2,2,4,4-tetramethylthietan-3-yl)amide, a potent sweetener.

DETAILED DESCRIPTION OF THE INVENTION

Although the Leuckart reaction is applicable to conversion of a wide variety of carbonyl compounds to amines, it does not, as might be expected work equally well with all carbonyl compounds. In general, for conversion of a given carbonyl compound to a desired amine, reaction conditions must be optimized. No set of reaction conditions is generally applicable. As described in the review article by Moore (loc. cit.), satisfactory conversion of many carbonyl compounds to amines occurs readily by heating a mixture of the selected carbonyl compound and the formic acid salt or formyl derivative of ammonia or the amine to be alkylated. The addition of various substances as catalysts, e.g., formic acid, ammonium formate, magnesium chloride or calcium chloride often improves the overall yield of a desired amine product and, in some instances, renders an otherwise inoperable or impractical Leuckart reaction, a satisfactory method of alkylation.

In the present invention boric acid or aluminum salts and hydrates thereof function as effective catalysts for preparation of 3-amino-2,2,4,4-tetramethylthietane via the Leuckart reaction. The favored aluminum salts are the chloride, sulfate and nitrate; and the hydrates of said salts.

The reaction comprises reductive alkylation of ammonia by the ketone 2,2,4,4-tetramethyl-3-oxothietane. Alternatively, it can be looked upon as the reductive amination of the ketone by ammonia.

When used as catalysts in the reaction described herein, magnesium chloride, calcium chloride, cerium chloride, barium chloride, titanium trichloride and titanium tetrachloride were found to produce yields of crude product similar to those produced by the catalysts of this invention. However, the product quality is significantly poorer than that produced by the catalysts of this invention. Thus, the catalysts of this invention simplify purification of the crude product and afford improved final yields of the desired pure amine. Zinc chloride and ferric chloride were ineffective as catalysts in said reaction as they were reduced to the metals under the reaction conditions used.

The addition of formic acid, ammonium chloride or small amounts of water (up to 5%) beyond that present in the reactants had a negligible effect upon the reaction.

The favored aluminum salts are desirably and preferably used in the form of their hydrates, e.g., $AlCl_3.6H_2O$, $Al_2(SO_4)_3.16H_2O$ and $Al(NO_3)_3.9H_2O$. They and boric acid are used in amounts ranging from about 2–20% w/w based upon the carbonyl compound. A favored amount of catalyst to ketone compound is 10% w/w.

The reaction must be run in a vessel that does not react with the reactants or products of the Leuckart reaction. Glass or Teflon lined vessels are appropriate vessels for the reaction.

It is desirable, for reasons of economy, to conduct the reaction at the lowest temperature which will produce the desired product in the best yield and purity. Temperatures of from about 140°–250° C. are used. The reaction time is, of course, a function of the temperature. In general, reaction times ranging from about 20 hours at the lower temperature range to about 4 hours at the upper temperature are sufficient to substantially complete the reaction. The reaction is normally carried out in a closed system; i.e., under pressure.

The ratio of ketone reactant to formamide is not critical. Molar ratios of 1:4 to 1:25 are generally used. Lower ratios tend to produce a higher level of by-products. Higher ratios appear to have little effect on the reaction.

The formyl derivative produced as intermediate in the reaction is conveniently hydrolyzed to the amine by refluxing with hydrochloric acid of concentration ranging from 1N to 12N (concentrated) until hydrolysis is complete. It is generally advantageous to isolate the intermediate formyl derivative prior to the hydrolysis step in order to obtain a higher quality product than is obtained by hydrolyzing the reaction mixture. A convenient isolation procedure comprises extraction of the reaction with a suitable solvent, e.g., methylene chloride, followed by removal of the solvent to provide a residue of the formamide derivative.

The invention is further illustrated by the following examples.

EXAMPLE 1

3-Amino-2,2,4,4-Tetramethylthietane

Formamide (8.0 g, 178 mmol), 2,2,4,4-tetramethyl-3-oxothietane (1.0 g, 6.933 mmol) and aluminum chloride hexahydrate (100 mg) were placed in a Teflon lined Parr bomb and heated at 170° C. for 18 hours. The reaction was then cooled and taken up in water (20 ml). The aqueous solution was extracted with methylene chloride (3×20 ml), the extracts combined and concentrated under reduced pressure. The residue was refluxed with 1N HCl (20 ml) for 4 hours, the reaction cooled and washed with methylene chloride (2×20 ml). It was then brought to pH 14 by addition of 6N sodium hydroxide and extracted with the methylene chloride (3×20 ml). The combined extracts were dried ($Na_2SO_4$) and concentrated to give 0.600 g (60%) of title product, verified by its $^1$H-NMR spectrum.

EXAMPLE 2

3-Amino-2,2,4,4-Tetramethylthietane

Formamide (4.0 g, 89 mmol), 2,2,4,4-tetramethyl-3-oxothietane (1.0 g, 6933 mmol) and boric acid (100 mg) were combined in a Teflon lined Parr bomb which was heated for 15 hours in a 175° C. oil bath. The reaction was cooled and the light brown mixture taken up in water (40 ml). The aqueous solution was extracted with methylene chloride (4×20 ml) and the combined extracts dried ($MgSO_4$) and evaporated under reduced pressure to a light brown oil (1.02 g). The residue was hydrolyzed and the hydrolyzate worked up according to the procedure of Example 1 to give the title product 650 mg (65%), verified by its $^1$H-NMR spectrum.

EXAMPLE 3

Repetition of the procedure of Example 1, but using the following catalysts in place of aluminum chloride hexahydrate provides 3-amino-2,2,4,4-tetramethylthietane:

$Al_2(SO_4)_3.16H_2O$
$AlCl_3$
$Al_2(NO_3)_3.9H_2O$
$Al_2(SO_4)_3$.

I claim:

1. A process for making 3-amino-2,2,4,4-tetramethylthietane which comprises
   (a) reacting formamide with 2,2,4,4-tetramethyl-3-oxothietane in the presence of boric acid or an aluminum salt at a temperature of from about 140°-250° C. in a closed system until reaction is substantially complete to produce the formamide derivative of 3-amino-2,2,4,4-tetramethylthietane; and,
   (b) hydrolyzing said formamide derivative.

2. The process according to claim 1 wherein the catalyst is boric acid.

3. The process according to claim 1 wherein the catalyst is a hydrate of the aluminum salt.

4. The process according to claim 3 wherein the catalyst is aluminum chloride hexahydrate.

5. The process according to claim 1 wherein the derivative is isolated from the reaction or to hydrolysis.

6. The process according to claim 4 wherein the formamide derivative is isolated from the reaction prior to hydrolysis.

* * * * *